(12) United States Patent
Alamin et al.

(10) Patent No.: US 8,029,541 B2
(45) Date of Patent: Oct. 4, 2011

(54) METHODS AND SYSTEMS FOR LATERALLY STABILIZED CONSTRAINT OF SPINOUS PROCESSES

(75) Inventors: Todd Alamin, Woodside, CA (US); Ian Bennett, San Francisco, CA (US); Colin Cahill, San Francisco, CA (US); Louis Fielding, San Carlos, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 877 days.

(21) Appl. No.: 11/777,366

(22) Filed: Jul. 13, 2007

(65) Prior Publication Data
US 2008/0177264 A1 Jul. 24, 2008

Related U.S. Application Data

(60) Provisional application No. 60/862,085, filed on Oct. 19, 2006.

(51) Int. Cl.
*A61B 17/70* (2006.01)

(52) U.S. Cl. .......................... 606/248; 606/250; 606/263

(58) Field of Classification Search .................... 606/53, 606/60, 246, 248, 249, 263, 326, 250–253, 606/278; 623/13.11, 13.13–13.2
See application file for complete search history.

(56) References Cited

U.S. PATENT DOCUMENTS

| | | |
|---|---|---|
| 3,648,691 A | 3/1972 | Lumb et al. |
| 4,246,660 A | 1/1981 | Wevers |
| 4,643,178 A | 2/1987 | Nastari et al. |
| 4,708,132 A | 11/1987 | Silvestrini |
| 4,743,260 A | 5/1988 | Burton |
| 4,772,286 A | 9/1988 | Goble et al. |
| 4,776,851 A | 10/1988 | Bruchman et al. |
| 4,794,916 A | 1/1989 | Porterfield et al. |
| 4,870,957 A | 10/1989 | Goble et al. |
| 4,955,910 A | 9/1990 | Bolesky |
| 4,966,600 A | 10/1990 | Songer et al. |
| 5,002,574 A | 3/1991 | May et al. |
| 5,011,484 A | 4/1991 | Breard |
| 5,092,866 A | 3/1992 | Breard et al. |
| 5,108,433 A | 4/1992 | May et al. |

(Continued)

FOREIGN PATENT DOCUMENTS

EP  0 322 334 A1  6/1989

(Continued)

OTHER PUBLICATIONS

Al Baz et al., "Modified Technique of Tension Band Wiring in Flexion Injuries of the Middle and Lower Cervical Spine," Spine, vol. 20, No. 11, 1995, p. 1241-1244.

(Continued)

*Primary Examiner* — Eduardo C Robert
*Assistant Examiner* — Lynnsy Schneider
(74) *Attorney, Agent, or Firm* — Wilson Sonsini Goodrich & Rosati

(57) ABSTRACT

A spinal implant for limiting flexion of the spine includes a tether structure for encircling adjacent spinal processes. Usually, a pair of compliance members will be provided as part of the tether structure for elastically limiting flexion while permitting an extension. A cross-member is provided between the compliance member or other portions of the tether structure to stabilize the tether structure and prevent misalignment after implantation.

15 Claims, 5 Drawing Sheets

U.S. PATENT DOCUMENTS

| | | | |
|---|---|---|---|
| 5,116,340 A | 5/1992 | Songer et al. | |
| 5,171,280 A | 12/1992 | Baumgartner | |
| 5,180,393 A | 1/1993 | Commarmond | |
| 5,282,863 A | 2/1994 | Burton | |
| 5,354,917 A | 10/1994 | Sanderson et al. | |
| 5,395,374 A | 3/1995 | Miller et al. | |
| 5,415,658 A | 5/1995 | Killpela et al. | |
| 5,415,661 A | 5/1995 | Holmes | |
| 5,449,361 A | 9/1995 | Preissman | |
| 5,456,722 A | 10/1995 | McLeod et al. | |
| 5,458,601 A | 10/1995 | Young, Jr. et al. | |
| 5,462,542 A | 10/1995 | Alesi, Jr. | |
| 5,496,318 A | 3/1996 | Howland et al. | |
| 5,540,698 A | 7/1996 | Preissman | |
| 5,562,737 A | 10/1996 | Graf | |
| 5,609,634 A * | 3/1997 | Voydeville | 623/13.11 |
| 5,628,756 A | 5/1997 | Barker, Jr. et al. | |
| 5,645,084 A | 7/1997 | McKay | |
| 5,645,599 A | 7/1997 | Samani | |
| 5,669,917 A | 9/1997 | Sauer et al. | |
| 5,672,175 A | 9/1997 | Martin | |
| 5,707,379 A | 1/1998 | Fleenor et al. | |
| 5,725,582 A * | 3/1998 | Bevan et al. | 606/263 |
| 5,902,305 A | 5/1999 | Beger et al. | |
| RE36,221 E | 6/1999 | Breard et al. | |
| 5,928,232 A | 7/1999 | Howland et al. | |
| 5,933,452 A | 8/1999 | Eun | |
| 5,935,133 A | 8/1999 | Wagner et al. | |
| 5,964,769 A | 10/1999 | Wagner et al. | |
| 5,989,256 A | 11/1999 | Kuslich et al. | |
| 6,053,921 A | 4/2000 | Wagner et al. | |
| 6,193,721 B1 | 2/2001 | Michelson | |
| 6,224,630 B1 | 5/2001 | Bao et al. | |
| 6,248,106 B1 | 6/2001 | Ferree | |
| 6,283,996 B1 | 9/2001 | Chervitz et al. | |
| 6,296,643 B1 * | 10/2001 | Hopf et al. | 606/263 |
| 6,312,431 B1 | 11/2001 | Asfora | |
| 6,322,279 B1 | 11/2001 | Yamamoto et al. | |
| 6,364,883 B1 | 4/2002 | Santilli | |
| 6,378,289 B1 | 4/2002 | Trudeau et al. | |
| 6,391,030 B1 | 5/2002 | Wagner et al. | |
| 6,395,018 B1 | 5/2002 | Castaneda | |
| 6,436,099 B1 | 8/2002 | Drewry et al. | |
| 6,451,019 B1 | 9/2002 | Zucherman et al. | |
| 6,468,309 B1 | 10/2002 | Lieberman | |
| 6,517,578 B2 | 2/2003 | Hein | |
| 6,558,389 B2 | 5/2003 | Clark et al. | |
| 6,582,433 B2 * | 6/2003 | Yun | 606/249 |
| 6,605,091 B1 | 8/2003 | Iwanski | |
| 6,616,669 B2 | 9/2003 | Ogilvie et al. | |
| 6,626,944 B1 | 9/2003 | Taylor | |
| 6,629,975 B1 | 10/2003 | Kilpela et al. | |
| 6,652,527 B2 | 11/2003 | Zucherman et al. | |
| 6,652,585 B2 | 11/2003 | Lange | |
| 6,656,185 B2 | 12/2003 | Gleason et al. | |
| 6,669,729 B2 | 12/2003 | Chin | |
| 6,682,533 B1 | 1/2004 | Dinsdale et al. | |
| 6,689,140 B2 | 2/2004 | Cohen | |
| 6,689,168 B2 | 2/2004 | Lieberman | |
| 6,695,852 B2 | 2/2004 | Gleason | |
| 6,712,819 B2 | 3/2004 | Zucherman et al. | |
| 6,716,245 B2 | 4/2004 | Pasquet et al. | |
| 6,761,720 B1 | 7/2004 | Senegas | |
| 6,828,357 B1 | 12/2004 | Martin et al. | |
| 6,835,205 B2 | 12/2004 | Atkinson et al. | |
| 6,899,716 B2 | 5/2005 | Cragg et al. | |
| 7,029,475 B2 | 4/2006 | Panjabi | |
| 7,163,558 B2 | 1/2007 | Senegas et al. | |
| 7,201,751 B2 | 4/2007 | Zucherman et al. | |
| 7,413,576 B2 | 8/2008 | Sybert et al. | |
| 7,452,351 B2 | 11/2008 | Miller et al. | |
| 7,458,981 B2 * | 12/2008 | Fielding et al. | 606/279 |
| 7,520,887 B2 * | 4/2009 | Maxy et al. | 606/248 |
| 7,524,324 B2 | 4/2009 | Winslow | |
| 7,553,320 B2 | 6/2009 | Molz, IV et al. | |
| 7,591,837 B2 | 9/2009 | Goldsmith | |
| 2002/0095154 A1 | 7/2002 | Atkinson et al. | |
| 2002/0147449 A1 * | 10/2002 | Yun | 606/61 |
| 2002/0151978 A1 | 10/2002 | Zacouto et al. | |
| 2003/0088251 A1 * | 5/2003 | Braun et al. | 606/73 |
| 2004/0024458 A1 | 2/2004 | Senegas et al. | |
| 2004/0106995 A1 | 6/2004 | Le Couedic et al. | |
| 2004/0116927 A1 | 6/2004 | Graf | |
| 2004/0117017 A1 | 6/2004 | Pasquet et al. | |
| 2004/0127989 A1 | 7/2004 | Dooris et al. | |
| 2004/0143268 A1 | 7/2004 | Falahee | |
| 2004/0167520 A1 | 8/2004 | Zucherman et al. | |
| 2004/0172132 A1 | 9/2004 | Ginn | |
| 2004/0215341 A1 | 10/2004 | Sybert et al. | |
| 2004/0243239 A1 | 12/2004 | Taylor | |
| 2005/0033435 A1 | 2/2005 | Belliard et al. | |
| 2005/0049708 A1 | 3/2005 | Atkinson et al. | |
| 2005/0123581 A1 | 6/2005 | Ringeisen et al. | |
| 2005/0131405 A1 | 6/2005 | Molz, IV et al. | |
| 2005/0154390 A1 | 7/2005 | Biedermann et al. | |
| 2005/0192581 A1 | 9/2005 | Molz et al. | |
| 2005/0216017 A1 * | 9/2005 | Fielding et al. | 606/74 |
| 2005/0267470 A1 | 12/2005 | McBride | |
| 2005/0267518 A1 | 12/2005 | Wright et al. | |
| 2006/0036324 A1 | 2/2006 | Sachs et al. | |
| 2006/0041259 A1 | 2/2006 | Paul et al. | |
| 2006/0064166 A1 * | 3/2006 | Zucherman et al. | 623/17.11 |
| 2006/0069447 A1 | 3/2006 | Disilvestro et al. | |
| 2006/0084976 A1 | 4/2006 | Borgstrom et al. | |
| 2006/0106381 A1 | 5/2006 | Ferree et al. | |
| 2006/0106397 A1 * | 5/2006 | Lins | 606/90 |
| 2006/0136060 A1 | 6/2006 | Taylor | |
| 2006/0142760 A1 | 6/2006 | McDonnell | |
| 2006/0149230 A1 | 7/2006 | Kwak et al. | |
| 2006/0195102 A1 | 8/2006 | Malandain | |
| 2006/0217726 A1 * | 9/2006 | Maxy et al. | 606/72 |
| 2006/0240533 A1 | 10/2006 | Sengupta et al. | |
| 2006/0241610 A1 | 10/2006 | Lim et al. | |
| 2006/0271055 A1 | 11/2006 | Thramann | |
| 2007/0010822 A1 | 1/2007 | Zalenski et al. | |
| 2007/0073293 A1 * | 3/2007 | Martz et al. | 606/61 |
| 2007/0083200 A1 * | 4/2007 | Gittings et al. | 606/61 |
| 2007/0213829 A1 | 9/2007 | Le Couedic et al. | |
| 2007/0233096 A1 | 10/2007 | Garcia-Bengochea | |
| 2007/0270828 A1 | 11/2007 | Bruneau et al. | |
| 2007/0299445 A1 | 12/2007 | Shadduck et al. | |
| 2008/0009866 A1 | 1/2008 | Alamin et al. | |
| 2008/0021466 A1 | 1/2008 | Shadduck et al. | |
| 2008/0027435 A1 | 1/2008 | Zucherman et al. | |
| 2008/0033552 A1 | 2/2008 | Lee et al. | |
| 2008/0045949 A1 | 2/2008 | Hunt et al. | |
| 2008/0051784 A1 | 2/2008 | Gollogly | |
| 2008/0097431 A1 | 4/2008 | Vessa | |
| 2008/0108993 A1 | 5/2008 | Bennett et al. | |
| 2008/0114357 A1 | 5/2008 | Allard et al. | |
| 2008/0125780 A1 | 5/2008 | Ferree | |
| 2008/0177298 A1 | 7/2008 | Zucherman et al. | |
| 2008/0183209 A1 | 7/2008 | Robinson et al. | |
| 2008/0262549 A1 | 10/2008 | Bennett et al. | |
| 2008/0281423 A1 | 11/2008 | Sheffer et al. | |
| 2008/0312693 A1 | 12/2008 | Trautwein et al. | |
| 2008/0319487 A1 | 12/2008 | Fielding et al. | |
| 2009/0030457 A1 | 1/2009 | Janowski et al. | |
| 2009/0082820 A1 | 3/2009 | Fielding et al. | |
| 2009/0118766 A1 | 5/2009 | Park et al. | |
| 2009/0198282 A1 | 8/2009 | Fielding et al. | |
| 2009/0264929 A1 | 10/2009 | Alamin et al. | |
| 2009/0264932 A1 | 10/2009 | Alamin et al. | |
| 2009/0270918 A1 | 10/2009 | Attia et al. | |
| 2010/0004701 A1 | 1/2010 | Malandain et al. | |
| 2010/0023060 A1 | 1/2010 | Bennett et al. | |
| 2010/0036424 A1 | 2/2010 | Fielding et al. | |
| 2010/0234890 A1 | 9/2010 | Alamin et al. | |
| 2010/0234894 A1 | 9/2010 | Alamin et al. | |
| 2010/0249839 A1 | 9/2010 | Alamin et al. | |

FOREIGN PATENT DOCUMENTS

| | | |
|---|---|---|
| EP | 0 743 045 A2 | 11/1996 |
| EP | 1 994 901 A1 | 11/2008 |
| FR | 2 681 525 A1 | 3/1993 |
| FR | 2 714 591 | 7/1995 |
| FR | 2 717 675 A1 | 9/1995 |

| | | |
|---|---|---|
| FR | 2 851 154 | 8/2004 |
| FR | 2874167 A1 * | 2/2006 |
| FR | 2 884 136 A1 | 10/2006 |
| WO | WO 01/28442 | 4/2001 |
| WO | WO 02/03882 A2 | 1/2002 |
| WO | WO 02/051326 | 7/2002 |
| WO | WO 02/071960 | 9/2002 |
| WO | WO 03/045262 | 6/2003 |
| WO | WO 2004/052246 | 6/2004 |
| WO | WO 2004/073532 | 9/2004 |
| WO | WO 2004/073533 | 9/2004 |
| WO | WO 2005/110258 A1 | 11/2005 |
| WO | WO 2008/051801 | 5/2008 |
| WO | WO 2008/051802 | 5/2008 |

OTHER PUBLICATIONS

Dickman et al., "Comparative Mechanical Properties of Spinal Cable and Wire Fixation Systems," Spine, vol. 22, No. 6, Mar. 15, 1997, pp. 596-604.

Garner et al., "Development and Preclinical Testing of a New Tension-Based Device for the Spine: the Loop system," European Spine Journal, vol. 11 (Suppl 2), 2002, pp. S186-191.

Heller, "Stability of Different Wiring Techniques in Segmental Spinal Instrumentation. An Experimental Study," Archives of Orthopedic and Trauma Surgery, vol. 117, No. 1-2, Nov. 1997, pp. 96-99.

Leahy et al., "Design of Spinous Process Hooks for Flexible Fixation of the Lumber Spine," Proceedings of the Institution of Mechanical Engineers, Part H, Journal of Engineering in Medicine, vol. 214, No. 5, Sep. 27, 2000, pp. 479-487.

Leahy et al., "Mechanical Testing of a Flexible Fixation Device for the Lumbar Spine," Proceedings of the Institution of Mechanical Engineers, Part H: Journal of Engineering in Medicine, vol. 214, No. 5, Sep. 27, 2000, pp. 489-495.

Minns et al., "Preliminary Design and Experimental Studies of a Novel Soft Implant for Correcting Sagittal Plane Instability in the Lumbar Spine," Spine, vol. 22, No. 16, Aug. 15, 1997, pp. 1819-1825.

Miyasaka et al., "Radiographic Analysis of Lumbar Motion in Relation to Lumbosacral Stability: Investigation of Moderate and Maximum Motion," Spine, vol. 25, No. 6, Mar. 15, 2000, pp. 732-737.

Papp et al., "An In Vitro Study of the Biomechanical Effects of Flexible Stabilization on the Lumbar Spine," Spine, vol. 22, No. 2, Jan. 15, 1997, pp. 151-155.

Shepherd et al., "Spinous Process Strength," Spine, vol. 25, No. 3, Feb. 1, 2000, pp. 319-323.

Shepherd, "Slippage of a Spinous Process Hook During Flexion in a Flexible Fixation System for the Lumbar Spine," Medical Engineering and Physics, vol. 23, No. 2, Mar. 2001, pp. 135-141.

Voydeville et al., "Ligamentoplastie Intervertebrale Avec Cale Souple dans Les Instabilites Lombaries" <<Intervertebral Ligamentoplasty with Flexible Wedge in Lumbar Instability,>>, Orthop Traumatol, vol. 2, 1992, pp. 259-264.

International Search Report and Written Opinion of PCT Application No. PCT/US2007/022191, dated Mar. 14, 2008, 13 pages total.

International Search Report and Written Opinion of PCT Application No. PCT/US2007/081835, dated Mar. 24, 2008, 8 pages.

Frymoyer et al., "An Overview of the Incidence and Costs of Low Back Pain" Orthrop. Clin. North Am., 1991;22: 263-271.

Abbott Spine, Wallis Surgical Technique [Product Brochure], 2006; 24 pages total.

Medtronic Sofamor Danek USA, Inc., DIAM™ System Implant; 2006 [Product Brochure]; downloaded from the Internet: <http://spineinfo.ru/~files/DIAMST.pdf>, 20 pages total.

International Search Report and Written Opinion of PCT Application No. PCT/US2007/081815, dated Jun. 23, 2008, 10 pages.

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

European Search Opinion of EP Patent Application No. 07863431.8, mailed Jun. 4, 2010, 5 pages total.

International Search Report and Written Opinion of PCT Application No. PCT/US2010/031615, mailed Jun. 18, 2010, 9 pages total.

International Search Report and Written Opinion of PCT Application No. PCT/US2010/031471, mailed Jul. 8, 2010, 13 pages total.

* cited by examiner

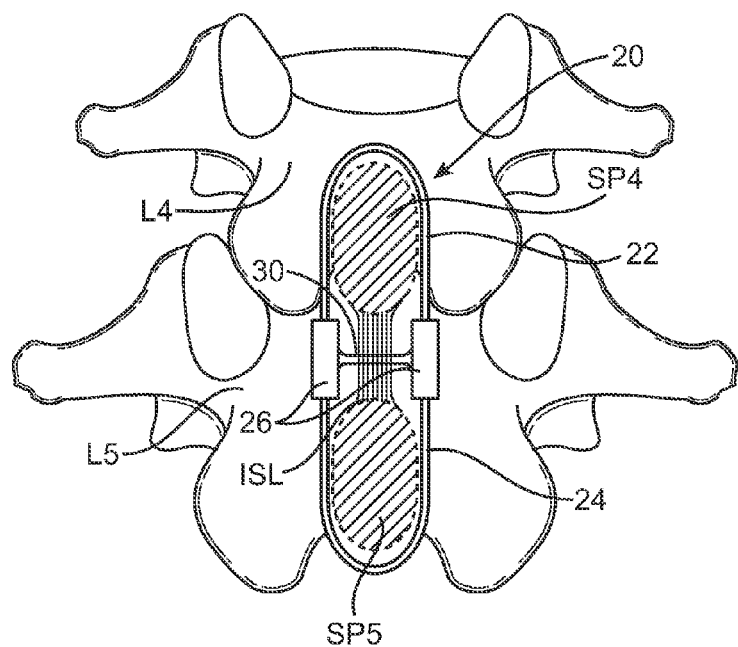
FIG. 5
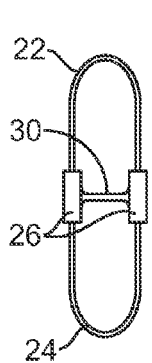 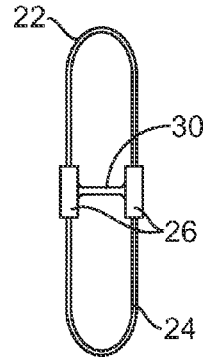
FIG. 6A    FIG. 6B
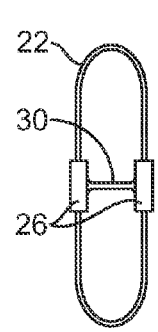 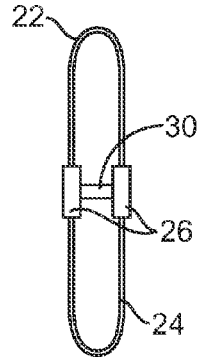
FIG. 7A    FIG. 7B
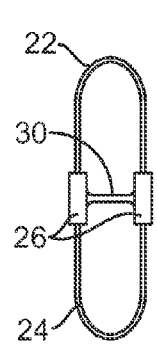 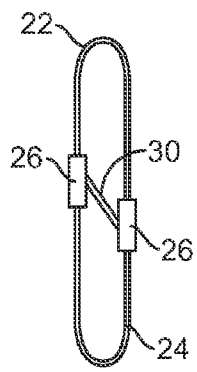
FIG. 8A    FIG. 8B

(54)
METHODS AND SYSTEMS FOR LATERALLY STABILIZED CONSTRAINT OF SPINOUS PROCESSES

CROSS-REFERENCES TO RELATED APPLICATIONS

This application claims the benefit of prior provisional application 60/862,085, filed on Oct. 19, 2006, the full disclosure of which is incorporated herein by reference.

BACKGROUND OF THE INVENTION

1. Field of the Invention

The present invention relates generally to medical methods and apparatus. More particularly, the present invention relates to methods and devices for restricting spinal flexion in patients having back pain or other spinal conditions.

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine (FIG. 1). Pain tends to be exacerbated when patients put their lumbar spines into flexion (i.e. by sitting or bending forward) and relieved when they put their lumbar spines into extension (i.e. arching backwards). Discogenic pain can be quite disabling, and for some patients, can dramatically affect their ability to work and otherwise enjoy their lives.

This pain experienced by patients with discogenic low back pain can be thought of as flexion instability and is related to flexion instability that is manifested in other conditions. The most prevalent of these is spondylolisthesis, a spinal condition in which abnormal segmental translation is exacerbated by segmental flexion.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebrae. Fusion is not usually recommended for discogenic pain because it is irreversible, costly, associated with high morbidity, and of questionable effectiveness. Despite its drawbacks, however, spinal fusion for discogenic pain remains common due to the lack of viable alternatives.

Recently, a less invasive and potentially more effective treatment for discogenic pain has been proposed. A spinal implant has been designed which inhibits spinal flexion while allowing substantially unrestricted spinal extension. The implant is placed over one or more adjacent pairs of spinal processes and provides an elastic restraint to the spreading apart of the spinal processes which occurs during flexion. Such devices and methods for their use are described in U.S. Patent Application 2005/02161017A1, published on Sep. 29, 2005, and having common inventors with the present application.

As illustrated in FIG. 2, an implant 10 as described in the '017 application, typically comprises an upper strap component 12 and a lower strap component 14 joined by a pair of compliant members 16. The upper strap 12 is shown disposed over the top of the spinous process SP4 of L4 while the lower strap 14 is shown extending over the bottom of the spinous process SP5 of L5. The compliance member 16 will typically include an internal element, such as a spring of rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinal processes which provides a force that resists flexion. The force increases, typically linearly with a non-variable spring constant, as the processes move further apart. Usually, the straps themselves will be essentially non-compliant so that the degree of elasticity or compliance may be controlled and provided solely by the compliance members 16.

Ideally, the compliance members 16 will remain horizontally aligned and spaced generally between the spinous processes SP4 and SP5, as shown generally in FIG. 3. In some instances, however, the desired symmetry may be lost if the implant structure 10 becomes circumferentially displaced about the spinous processes SP4 and SP5, as shown in FIG. 4. Such displacement can affect the ability of the implant to provide a uniform, symmetric elastic force to inhibit flexion of the spinous processes in accordance with the desired treatment.

For these reasons, it would be desirable to provide improved spinal implants and methods for their use in inhibiting flexion in patients suffering from discogenic pain. It would be particularly desirable if the improved devices would provide the desired elastic forces to the spinous processes without displacement or loss of symmetry of the device over time. At least some of these objectives will be met by the inventions described hereinbelow.

2. Description of the Background Art

US 2005/0216017A1 has been described above. Other patents and published applications of interest include: U.S. Pat. Nos. 4,966,600; 5,011,494; 5,092,866; 5,116,340; 5,282,863; 5,395,374; 5,415,658; 5,415,661; 5,449,361; 5,456,722; 5,462,542; 5,496,318; 5,540,698; 5,609,634; 5,645,599; 5,725,582; 5,902,305; Re. 36,221; 5,928,232; 5,935,133; 5,964,769; 5,989,256; 6,053,921; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; Published U.S. Patent Application Nos. US 2002/0151978; US 2004/0024458; US 2004/0106995; US 2004/0116927; US 2004/0117017; US 2004/0127989; US 2004/0172132; US 2005/0033435; US 2005/0049708; US 2006/0069447; Published PCT Application Nos. WO 01/28442 A1; WO 02/03882 A2; WO 02/051326 A1; WO 02/071960 A1; WO 03/045262 A1; WO 2004/052246 A1; WO 2004/073532 A1; and Published Foreign Application Nos. EP 0322334 A1; and FR 2 681 525 A1.

BRIEF SUMMARY OF THE INVENTION

The present invention provides spinal implants and methods for restricting spinal flexion for the treatment of discogenic pain and other spinal conditions, such as spondylolisthesis, where the physician desires to control spinal flexion. The spinal implants comprise a tether structure adapted to encircle at least two spinous processes, where at least a portion of the tether structure is adapted to elastically elongate to apply tension to the spinous processes as the spine undergoes flexion, i.e. as the spinous processes move apart as the patient leans forward. The tether structure may comprise any of the particular structures described in detail in U.S. patent application Ser. No. 11/076,469, filed on Mar. 9, 2005, and published as US 2005/0216017 A1, the full disclosure of which is incorporated herein by reference.

In particular, in the simplest embodiments, the tether structure may comprise a single, continuous loop of material wherein all or a portion of the loop is formed of a compliant material to provide the desired elasticity. More commonly, the tether structure will comprise one or more band segments joined by one or more compliance members, where the band(s) are typically non-distensible and the compliance member(s) provide for the desired elasticity. In some instances, the compliance members may comprise spring or other elements which provide an elastic tensioning force where the band member(s) are attached to opposite ends of the spring member. In other instances, the compliance members could include elastomeric or other compression elements, where the band member(s) are attached to opposed sides of the compressive elements so that the elasticity is provided by compression on the compression member.

In preferred embodiments, the tether structure will comprise a pair of band members joined by a pair of compliance members, where an upper band member will be placed over the superior surface of an upper spinous process and the lower band member will be placed over an inferior surface of the lower spinous process. The compliance members will be generally horizontally aligned across the region between the upper and lower spinous processes. A connecting mechanism may loin the pair of band members.

In a particular aspect of the present invention, the spinal implants will include at least one cross-member coupled to opposed portions of the tether structure, where the cross-member is positioned to lie between the spinous processes when the tether structure encircles the processes as described above. In specific embodiments, the cross-member will extend between the horizontally aligned compliance members, but in other embodiments a cross-member could be coupled to other portions or components of the tether structure, including the band or loop elements which are disposed over the spinous processes.

The cross-member(s) functions to stabilize the tether structure after the tether structure has been implanted over the spinous processes. In particular, the cross-member(s) will help maintain the symmetry of the device so that it does not circumferentially rotate or migrate over the spinous processes, which is a potential problem when the tether includes one or more compliance members. In addition, the cross-member(s) may optionally maintain the lateral spacing between the two sides of the device, such as between a pair of horizontally aligned compliance members. The cross-member(s) may further prevent or inhibit vibration or sinusoidal movement of the device which may result from dynamic and/or cyclic loading.

In addition to the stabilization functions, a cross-member may help in initial placement and positioning of the tether structure. For example, a tether structure including a pair of horizontally aligned compliance members may be introduced and assembled in situ, where the cross-member helps establish the initial horizontal alignment between the compliance members. Alternatively, when no compliance members are to be used, the cross-member could itself provide for connection points for attaching upper and lower band segments. Additionally, the cross-member(s) can create pivot points to allow rotation or pivoting of the band relative to the cross-member(s) as well as the other band segments.

The cross-member(s) may have a wide variety of particular configurations. The most common cross-member(s) will have generally rigid structures, e.g. in the form of a rod, bar, beam, or the like. In other instances, however, the cross-member(s) may be relatively flexible, in some cases being in the form of a wire, ribbon, string, spring, suture, or the like. In still other configurations, the cross-member(s) may be linearly compressible, but not extensible, in order to allow for a controlled degree of inward motion of the tether structure after it has been placed. In still other configurations, the cross-member(s) may be linearly non-compressible, but allow for a small degree of axial extension in order to prevent inward motion or intrusion of the tether structure into the region between the spinous processes.

There are also a variety of ways in which the cross-member(s) may be attached to the tether structure. Typically, the cross-member(s) will be attached to opposed compliance members (usually to housings of the compliance member subassemblies as shown in the '017 application previously incorporated by reference), where the attachment can be rigid, semi-rigid, pivotal, or the like. In a first exemplary embodiment, the cross-member is rigidly attached to a pair of compliance members in a generally H-shaped configuration. In other instances, the connections may be pivotal or non-rigid, as mentioned above. Still further, the cross-member can be completely flexible which would allow for a small degree of motion between the compliance members after implantation.

While most embodiments of the present invention will employ only a single cross-member, in other embodiments two or more cross-members may be used. For example, a pair of cross-members may be positioned between opposed portions of the tether structure, where an upper cross-member is located immediately below the inferior surface of the upper spinal process, while the lower cross-member is positioned immediately adjacent to a superior surface of the lower spinal process. Alternatively, such cross-member pairs may be positioned more closely to the compliance members, e.g. where they lie immediately above and below the compliance members. In still other embodiments, the cross-members may be slidably attached to the bands or other portions of the tether structure so that the cross-members may move in response to a force applied by the spinous processes or otherwise.

In all the embodiments of the present invention, it will be desirable that the cross-member(s) provide little or no resistance to extension, i.e. motion of the adjacent spinous processes toward one another. When the cross-member consists of a single rod, bar, structure, or other flexible element extending between exposed portions of the tether structure, the cross-member will usually have a very small vertical height (typically less than 6 mm, usually in the range from 1 mm to 3 mm), and it is unlikely that the cross-member would contact either spinous process even in an extreme degree of extension, so long as the cross-member is located at a position which is equally spaced apart from the two spinous processes. In other instances, however, the cross-member could have a larger cross-sectional profile which might contact either or both spinous processes as the spine undergoes extension. In such cases, it is desirable that the cross-member be collapsible or otherwise provide minimum force against either or both processes.

Usually, the cross-member will be implanted through the interspinous ligament which extends between the upper and lower spinous processes. In such instances, it is desirable that the cross-member itself have a relatively low profile to permit passage through the ligament with minimum trauma. Often, it will be desirable to have the cross-member detachable from at least one of the opposed tether structure components so that the cross-members or other portions of the tether structure do not need to be passed through the interspinous ligament.

In another aspect of the present invention, methods for stabilizing spinal flexion comprise positioning a continuous tether structure over a pair of adjacent spinous processes on adjacent vertebrae to elastically restrict flexion. The tether structure will be positioned and have mechanical properties which will elastically tension the processes when the processes are in flexion. In accordance with the principles of the present invention, opposed portions of the tether structure are mechanically coupled, usually through the interspinous ligament, in order to stabilize the structure, particularly to inhibit circumferential displacement of the tether structure over time.

In the exemplary embodiments, the opposed portions of the tether structure will comprise compliance members, and it will be the compliance members which are mechanically coupled to stabilize the structure in situ. Typically, the compliance members will be connected by at least one cross-member wherein said at least one cross-member is fixably or non-fixably attached to the compliance members. In some embodiments, one end of the cross-member may be fixably attached to one compliance member while the other member is non-fixably attached to the other compliance member. The cross-member itself may be rigid, semi-rigid, or non-rigid, and in all instances the cross-member will provide no significant inhibition of spinal extension. Preferably, the cross-member will pass through the interspinous ligament without significant damage or compromise to its integrity.

Optionally, one or more additional tether structures may be implanted around other pair(s) of spinous processes in the manner described above.

BRIEF DESCRIPTION OF THE DRAWINGS

FIG. 5 illustrates a first embodiment of a spinal implant having a cross-member in accordance with the principles of the present invention.

FIGS. 6A and 6B illustrate the spinal implant of FIG. 5 having a rigid cross-member.

FIGS. 7A and 7B illustrate the spinal implant of FIG. 5 having a semi-rigid cross-member.

FIGS. 8A and 8B illustrate the cross-member of FIG. 5 having an elastic cross-member.

DETAILED DESCRIPTION OF THE INVENTION

Figure 1:
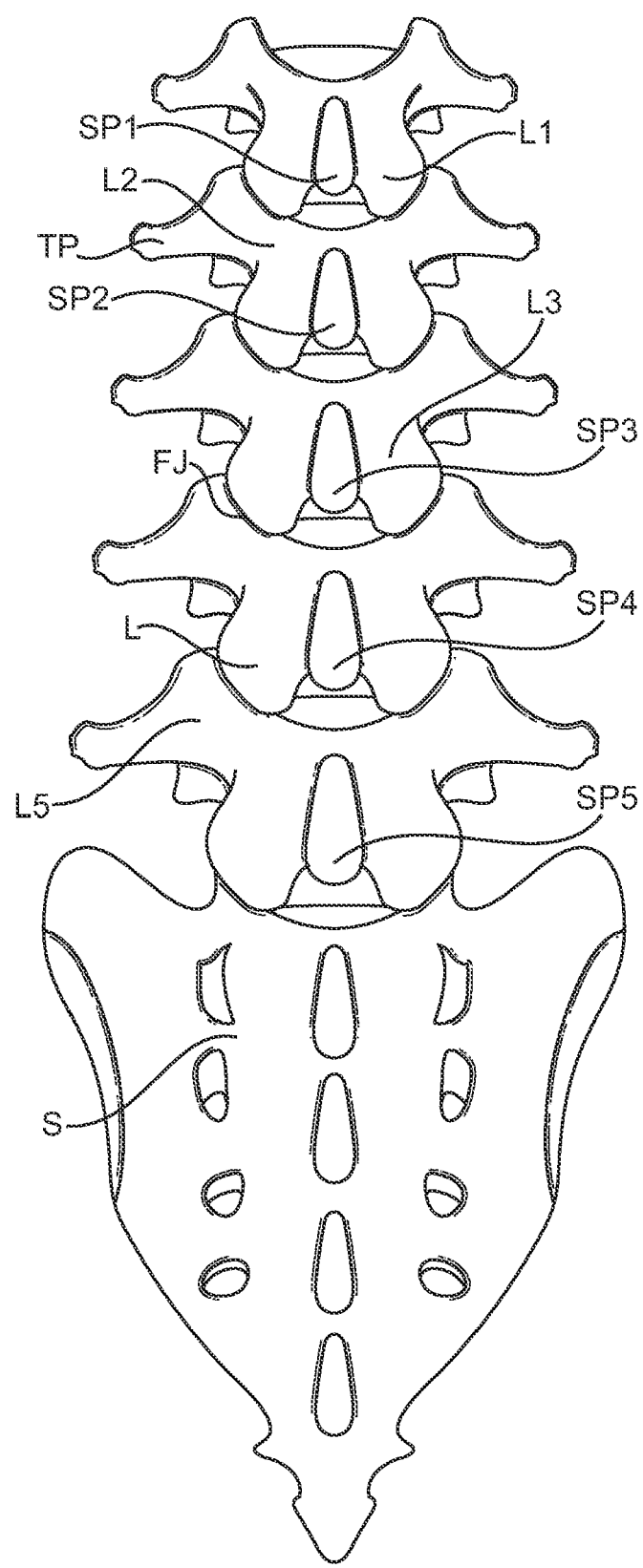
FIG. 1 is a schematic diagram illustrating the lumbar region of the spine including the spinal processes (SP), facet joints (FJ), lamina (L), transverse processes (TP), and sacrum (S).
Figure 2:
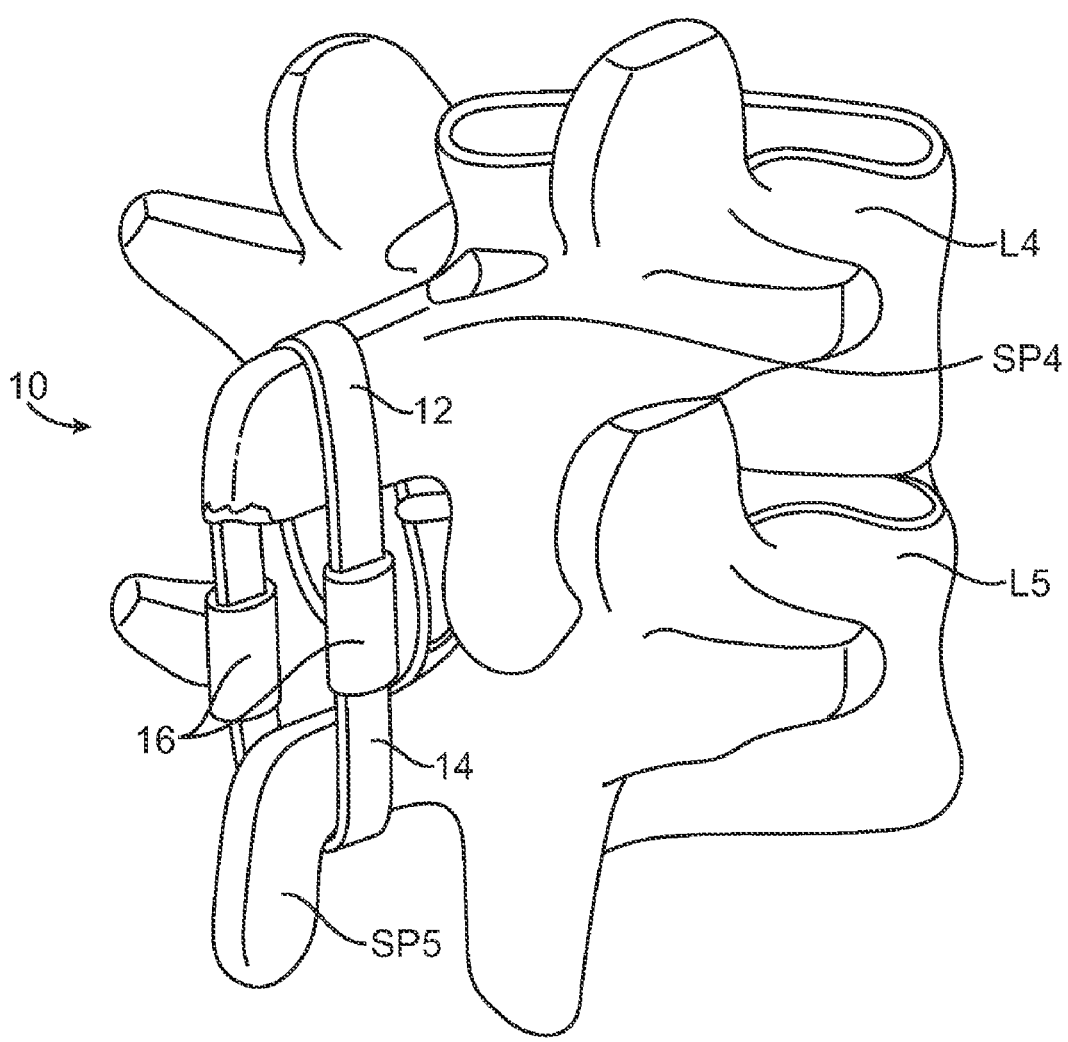
FIG. 2 illustrates a spinal implant of the type described in US 2005/0216017A1.
Figure 3:
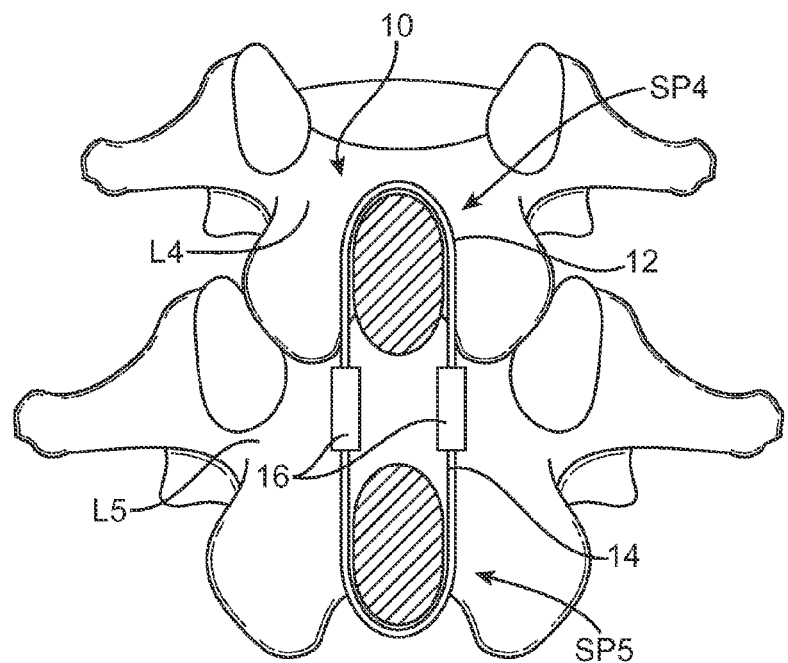
FIGS. 3 and 4 illustrate how the spinal implant of FIG. 2 can become misaligned over time.
Figure 4:
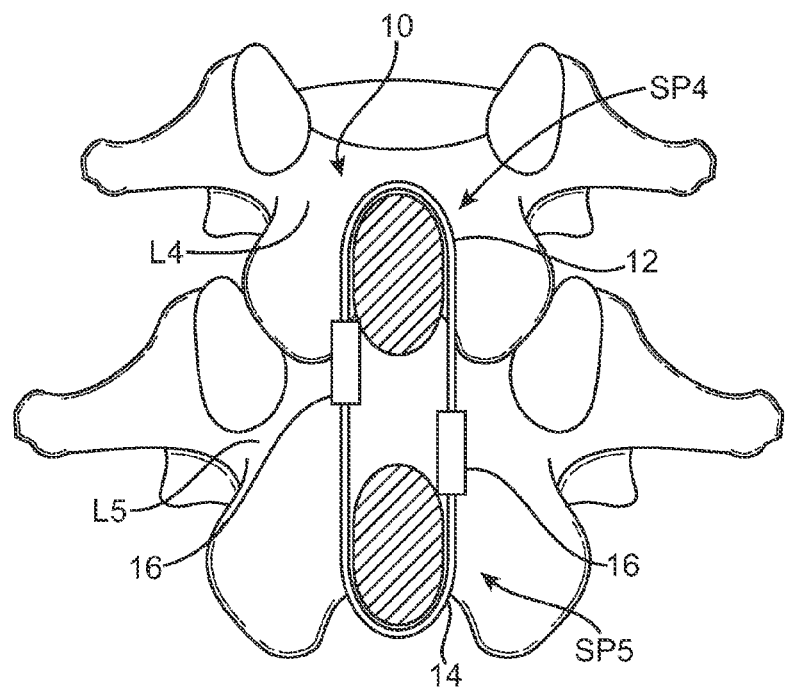

Referring now to FIG. 5, a spinal implant 20 constructed in accordance with the principles of the present invention comprises an upper strap 22, a lower strap 24, and a pair of compliance members 26 joining the upper and lower straps. Typically, the upper and lower straps 22 and 24 will be non-distensible but will be joined to the compliance members 26 so that they can be expanded from a constricted configuration, as shown in broken line, when the patient's spine is in a neutral position between flexion and extension, to an expanded configuration (shown in full line) when the patient's spine is in flexion. The compliance members 26 will provide a force which acts against the extension of the spinous processes, as generally described in prior patent application U.S. 2005/0216017, which has been previously incorporated herein by reference. In particular accordance with the present invention, a cross-member 30 extends between and joins the compliance members 26. The cross-member 30 passes through the interspinous ligament ISL.

As shown in FIGS. 6A and 6B, the cross-member 30 may be rigid and be rigidly attached to the compliance members 26 in a generally H-shaped configuration so that the compliance members do not shift relative to each other even when the upper and lower bands 22 and 24 are pulled apart, as shown in FIG. 6B. Alternatively, the cross-member 30 may be semi-rigid (or semi-compliant) so that it will undergo compression when the upper band 22 is pulled away from the lower band 24, as shown in FIG. 7B. In a third embodiment, the cross-member 30 may be entirely elastic, as shown in FIGS. 8A and 8B. In such instances, the cross-member 30 will allow the compliance members 26 to vertically displaced relative to each other by a controlled amount, as shown in FIG. 8B.

Figure 9:
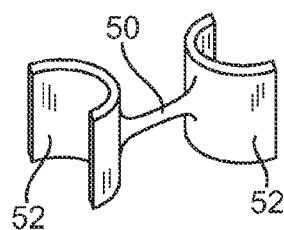
FIG. 9 illustrates a specific embodiment of a cross-member useful in the apparatus and methods of the present invention.
Figure 10:
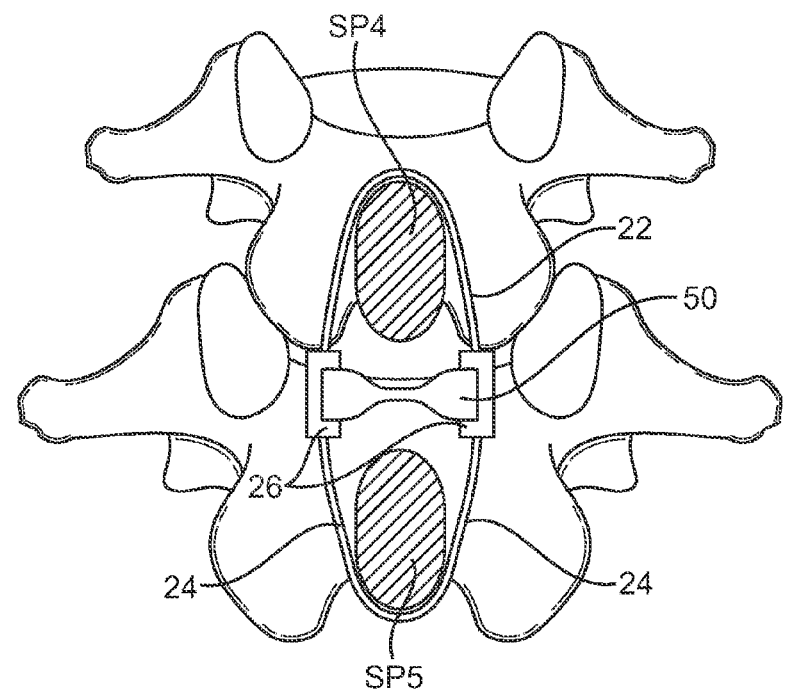
FIG. 10 illustrates the cross-member of FIG. 9 in an implant.

FIG. 9 illustrates an exemplary cross-member 50 which can be coupled to compliance members 26, as shown in FIG. 10. The cross-member 50 is a rigid structure which may be attached (and optionally detached) from the compliance member during implantation of the spinal implant. End portions 52 of the cross-member are shaped and adapted to be attached to the cylindrical bodies of the compliance members. Other shapes and structures for selective attachment and detachment of the cross-member are, of course, readily available.

Figure 11:
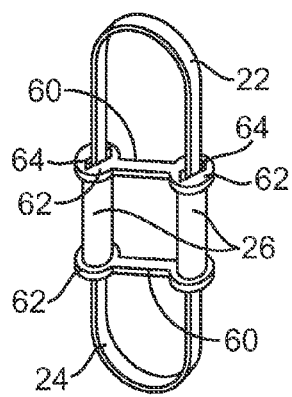
FIG. 11 illustrates an embodiment of the present invention having a pair of cross-members.
Figure 12:
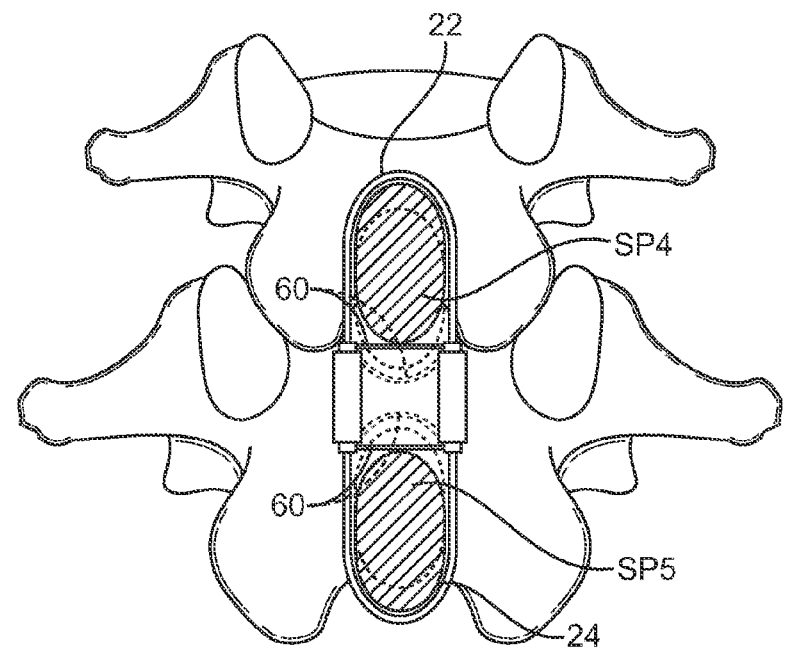
FIG. 12 illustrates the spinal implant of FIG. 11 in an implant.

A pair of cross-members 60 are illustrated in FIG. 11. The cross-members 60 have endpieces 62, each having a slot 64 which receives the corresponding band 22 or 24. Cross-members 60 can thus be disposed directly over the upper and lower surfaces of the compliance members 26, as shown in FIG. 12. Usually, cross-members 60 will themselves be compliant in order to avoid inhibiting of extension of the spinal processes SP4 and SP5, as shown in broken line in FIG. 12.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A spinal implant comprising:
   a tether structure comprising upper and lower straps, and a pair of compliance members attaching the upper and the lower straps together, wherein the tether structure is adapted to encircle at least two spinous processes, and the compliance members elastically elongate to apply an axially oriented tension on the spinous processes as the spine undergoes flexion; and
   at least one cross-member coupled to opposed portions of the tether structure and positioned to lie between the spinous processes when the tether structure encircles said processes, wherein the cross-member is configured to allow extension of the spine to remain substantially unrestricted, wherein the cross-member is configured to bear minimal axial load when the spine is in extension, and wherein the at least one cross-member has a profile suitable for passage through an interspinous ligament, and wherein the cross-member is linearly compressible but not extensible such that the cross-member undergoes compression when the upper strap is pulled away from the lower strap thereby controlling inward motion of the tether structure.

2. A spinal implant as in claim 1, wherein the pair of compliance members are opposed with one another and positioned to lie on opposite sides of the spinous processes when the tether structure encircles said processes.

3. A spinal implant as in claim 2, wherein the cross-member is attached to and extends between said compliance members.

4. A spinal implant as in claim 2, wherein the at least one cross-member is attached at a location on said tether structure adjacent to said compliance members.

5. A spinal implant as in claim 2, wherein said cross-member is semi-rigid and fixedly attached to the said compliance members so that said compliance members and said cross-member comprise a semi-rigid H-structure.

6. A spinal implant as in claim 1, wherein the cross-member does not limit the motion of the spinous processes.

7. A spinal implant as in claim 1, wherein the cross-member is semi-rigid.

8. A spinal implant as in claim 1, wherein the upper and the lower straps are substantially non-distensible.

9. A method for restricting spinal flexion in a spine, said method comprising:
 positioning an upper strap of a tether structure over an upper spinous process and a lower strap of the tether structure over a lower spinous process, wherein the spinous processes are on a pair of adjacent vertebrae, wherein the upper strap and the lower strap are joined together with a pair of compliance members, and wherein the compliance members provide an axially oriented tension on the upper and the lower spinous processes when the spine undergoes flexion; and
 mechanically coupling opposed portions of the tether structure with a cross member that passes through an interspinous space to inhibit circumferential displacement of the tether structure over time, wherein the cross-member bears minimal axial load when the spine is in extension, wherein the cross-member allows extension of the spine to remain substantially unrestricted, and wherein the at least one cross-member has a profile suitable for passage through an interspinous ligament, and
 wherein the cross-member is linearly compressible but not extensible such that the cross-member undergoes compression when the upper strap is pulled away from the lower strap thereby controlling inward motion of the tether structure.

10. A method as in claim 9, wherein the compliance members are connected with the cross-member.

11. A method as in claim 10, wherein the cross-member is fixedly attached to the compliance members.

12. A method as in claim 9, wherein the cross-member is semi-rigid.

13. A method as in claim 9, wherein the integrity of the interspinous ligament is not significantly compromised.

14. A method as in claim 9, further comprising positioning at least one additional continuous tether structure over spinous processes on another pair of adjacent vertebrae and mechanically coupling opposed portions of the tether structure through the interspinous space.

15. A method as in claim 9, wherein the upper and the lower straps are substantially non-distensible.

* * * * *